US008940933B2

(12) United States Patent
Shirasawa et al.

(10) Patent No.: US 8,940,933 B2
(45) Date of Patent: Jan. 27, 2015

(54) METHOD FOR PRODUCING POLYOXYALKYLENE ALKYL ETHER CARBOXYLIC ACID AND SALT THEREOF

(75) Inventors: Takeshi Shirasawa, Wakayama (JP); Yasuo Amishige, Wakayama (JP); Kaoru Omae, Wakayama (JP); Akira Matsunaga, Wakayama (JP); Akira Sakaguchi, Wakayama (JP)

(73) Assignee: Kao Corporation, Tokyo (JP)

( * ) Notice: Subject to any disclaimer, the term of this patent is extended or adjusted under 35 U.S.C. 154(b) by 296 days.

(21) Appl. No.: 13/519,703

(22) PCT Filed: Dec. 22, 2010

(86) PCT No.: PCT/JP2010/073079
§ 371 (c)(1),
(2), (4) Date: Aug. 6, 2012

(87) PCT Pub. No.: WO2011/081063
PCT Pub. Date: Jul. 7, 2011

(65) Prior Publication Data
US 2012/0296115 A1    Nov. 22, 2012

(30) Foreign Application Priority Data
Dec. 28, 2009  (JP) ................................ 2009-297083

(51) Int. Cl.
C07C 51/295    (2006.01)
C07C 59/305    (2006.01)
B01J 23/644    (2006.01)
C07C 51/235    (2006.01)

(52) U.S. Cl.
CPC ........... B01J 23/6447 (2013.01); C07C 51/235 (2013.01)
USPC .......................................... 562/539; 562/587

(58) Field of Classification Search
CPC ....................................................... C07C 51/235
See application file for complete search history.

(56) References Cited

U.S. PATENT DOCUMENTS

| | | | |
|---|---|---|---|
| 3,342,858 A * | 9/1967 | Fuhrmann et al. ............. | 562/537 |
| 3,890,381 A | 6/1975 | Kiyoura et al. | |
| 4,214,101 A | 7/1980 | Miya et al. | |
| 4,233,460 A | 11/1980 | Willis et al. | |
| 4,976,893 A | 12/1990 | Leupold | |
| 5,223,642 A | 6/1993 | Schonwalder | |
| 5,292,940 A * | 3/1994 | Carduck et al. ............... | 562/538 |
| 5,689,012 A | 11/1997 | Pazos et al. | |
| 2007/0112208 A1 | 5/2007 | Le-Khac | |
| 2012/0296115 A1 | 11/2012 | Shirasawa et al. | |

FOREIGN PATENT DOCUMENTS

| | | |
|---|---|---|
| CA | 2080478 A1 | 10/1991 |
| EP | 0018681 A2 | 11/1980 |
| EP | 0039111 A1 | 11/1981 |
| EP | 0304763 A1 | 3/1989 |
| JP | 56-169644 A | 12/1981 |
| JP | 61-293948 A | 12/1986 |
| JP | 62-198641 A | 9/1987 |
| JP | 62-269746 A | 11/1987 |
| JP | 63-6056 B2 | 2/1988 |
| JP | 63-211251 A | 9/1988 |
| JP | 1-102035 A | 4/1989 |
| JP | 1-146840 A | 6/1989 |
| JP | 1-149752 A | 6/1989 |
| JP | 4-221339 A | 8/1992 |
| JP | 4-342542 A | 11/1992 |
| JP | 5-503686 A | 6/1993 |
| JP | 7-291893 A | 11/1995 |
| JP | 2011-136933 A | 7/2011 |
| WO | WO 2005/103116 A1 | 11/2005 |

OTHER PUBLICATIONS

Walas, Chemical Process Equipment Selection and Design, 1990, Butterworth-Heinemann, Boston, MA, pp. 549-610.*
International Search Report issued in PCT/JP2010/073079, mailed on Mar. 22, 2011.
Written Opinion of the International Searching Authority issued in PCT/JP2010/073079, mailed on Mar. 22, 2011.
Extended European Search Report dated Aug. 12, 2013 for European Application No. 10840920.2.
The Notification of Second Office Action (including English translation), dated Apr. 30, 2014, issued in the corresponding Chinese Patent Application No. 201080059852.8.
Walas, Chinese version of "Reaction Kinetics for Chemical Engineers," McGraw-Hill Book Company, Chapter 4, Figs. 4-1 to 4-3, 1959 (4 pages).
International Preliminary Report on Patentability and Written Opinion of the International Searching Authority dated Aug. 14, 2012, for Application No. PCT/JP2010/073079.

* cited by examiner

*Primary Examiner* — Paul A Zucker
(74) *Attorney, Agent, or Firm* — Birch, Stewart, Kolasch & Birch, LLP

(57) ABSTRACT

The present invention provides a method for producing polyoxyalkylene alkyl ether carboxylic acid and a salt thereof, including supplying polyoxyalkylene alkyl ether, oxygen, and water to a continuous stirred tank reactor containing a noble metal catalyst to oxidize the polyoxyalkylene alkyl ether with oxygen, in which the molar ratio of the salt of polyoxyalkylene alkyl ether carboxylic acid to the polyoxyalkylene alkyl ether in the continuous stirred tank reactor is controlled to 0.33 to 49.

16 Claims, No Drawings

METHOD FOR PRODUCING POLYOXYALKYLENE ALKYL ETHER CARBOXYLIC ACID AND SALT THEREOF

FIELD OF THE INVENTION

The present invention relates to a method for producing polyoxyalkylene alkyl ether carboxylic acid and a salt thereof.

BACKGROUND OF THE INVENTION

Salts of polyoxyalkylene alkyl ether carboxylic acid are compounds produced by substituting polyoxyalkylene alkyl ether with carboxylic acid at the terminal end of the ether, and are known as a useful surfactant used in cosmetics, emulsifiers, solubilizers, dispersants, gelling agents, and detergent bases, and the like. The salts can be modified in properties by changing pH. These salts have good stability against hard water. Aqueous solutions thereof are stable to various polyvalent metal ions such as an aluminum ion, gentle to the skin, and have small inhibitory effects on enzymes. The salts are thus expected to have various applications.

There have been various known methods for producing a salt of polyoxyalkylene alkyl ether carboxylic acid. One of the methods in which polyoxyalkylene alkyl ether is oxidized with oxygen in the presence of a noble metal catalyst is known (JP-A 56-169644, JP-A 62-198641, and JP-A 62-269746). JP-A 01-146840 describes addition of an ether carboxylic acid to a polyalkoxy alcohol or a fatty alcohol alkoxylate in oxidation of the polyalkoxy alcohol or the fatty alcohol alkoxylate to produce the ether carboxylic acid.

SUMMARY OF THE INVENTION

The present invention relates to a method for producing a polyoxyalkylene alkyl ether carboxylic acid and a salt thereof, comprising continuously supplying polyoxyalkylene alkyl ether, oxygen, and water to a continuous stirred tank reactor in the presence of a noble metal catalyst to control the reaction in order to have the molar ratio of the salt of polyoxyalkylene alkyl ether carboxylic acid to the polyoxyalkylene alkyl ether in the reactor within the range of 0.33 to 49.

The present invention also relates to a method for producing polyoxyalkylene alkyl ether carboxylic acid and a salt thereof, including supplying a polyoxyalkylene alkyl ether and oxygen to a continuous stirred tank reactor in the presence of a noble metal catalyst and controlling the reaction rate of the polyoxyalkylene alkyl ether in the reactor within the range of 25 to 98%.

DETAILED DESCRIPTION OF THE INVENTION

Oxidation of polyoxyalkylene alkyl ether with oxygen in the presence of a noble metal catalyst generally takes a relatively long time to achieve a certain reaction rate (e.g., about 60%). JP-A 01-146840 describes a method capable of reducing the reaction time, but does not fully refer to specific conditions and the like for efficient production of polyoxyalkylene alkyl ether carboxylic acid having high quality in color and the like for a short time. In particular, there is no special suggestion about efficient means for production of polyoxyalkylene alkyl ether carboxylic acid having a good color, using an industrially practical apparatus for continuous production of ether carboxylic acid, such as a continuous stirred tank reactor.

The present invention provides a method for efficiently producing polyoxyalkylene alkyl ether carboxylic acid and a salt thereof having high quality using a continuous stirred tank reactor.

The present invention provides a method that can efficiently produce polyoxyalkylene alkyl ether carboxylic acid and a salt thereof having a high quality in color and the like, using a continuous stirred tank reactor.

In the present invention, polyoxyalkylene alkyl ether and oxygen are preferably supplied to a liquid phase containing a noble metal catalyst in the continuous stirred tank reactor. In the present invention, an alkali material and water are preferably further supplied to the liquid phase.

One preferred embodiment of the present invention is the method for producing polyoxyalkylene alkyl ether carboxylic acid and a salt thereof, wherein the polyoxyalkylene alkyl ether is catalytically oxidized by supplying oxygen to form polyoxyalkylene alkyl ether carboxylic acid and a salt thereof, and the amount of dissolved oxygen in the liquid phase in the continuous stirred tank reactor to which the oxygen is supplied is kept to be more than 0 ppm and not more than 1 ppm.

Another preferred embodiment of the present invention is the method for producing polyoxyalkylene alkyl ether carboxylic acid and a salt thereof, wherein the polyoxyalkylene alkyl ether is catalytically oxidized by supplying oxygen to the liquid phase containing the polyoxyalkylene ether and the alkali material to form polyoxyalkylene alkyl ether carboxylic acid and a salt thereof, and the amount of dissolved oxygen in the liquid phase in the continuous stirred tank reactor to which the oxygen is supplied is kept to be more than 0 ppm and not more than 1 ppm.

The present invention includes controlling the reaction rate of the polyoxyalkylene alkyl ether in the reactor within the range of 25 to 98%.

In the present invention, a noble metal catalyst may be used. According to the present invention, polyoxyalkylene alkyl ether carboxylic acid and a salt thereof can be produced at a high conversion rate even with a reduced amount of the catalyst. The method of the present invention is thus highly advantageous in industry.

The polyoxyalkylene alkyl ether of the invention is preferably a compound represented by formula (I):

$$RO-(AO)_n-H \qquad (I)$$

wherein, R represents a hydrocarbon group having 4 to 36 carbon atoms; AO represents an alkyleneoxy group having 2 to 4 carbon atoms; and n represents an average addition mole number ranging from 1 to 100.

In formula (I), R preferably represents a hydrocarbon group having 4 to 30 carbon atoms, and n is preferably a number of 1 to 100. The polyoxyalkylene alkyl ether carboxylic acid of formula (I) can have any appropriate structure determined according to desired properties and an intended use thereof. From the viewpoint of properties as detergent base, R preferably has 10 to 14 carbon atoms. Examples of the hydrocarbon group as R include an alkyl group and an alkenyl group. R may be a linear or branched, primary or secondary group. From the viewpoints of versatility as a raw material and economic efficiency, AO preferably represents an ethyleneoxy group having 2 carbon atoms, and preferably not less than 80% by mole of the total of AOs are ethyleneoxy groups. From the viewpoint of fluidity in a reaction mixture, n is preferably a number of 1 to 10. Of course, a mixture of compounds having different structures, collectively represented by formula (I), can be reacted.

Examples of the linear or branched alkyl group as R include various pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, and docosyl groups. Examples of the linear or branched alkenyl group as R include various vinyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, henicosenyl, and docosenyl groups. Examples of an aliphatic hydrocarbon group having a cyclic structure include groups of cyclooctyl, cyclodecyl, cyclododecyl, cyclooctenyl, cyclodecenyl, cyclododecenyl, 2-(cyclohexyl)ethyl, 3-(cyclohexyl)propyl, 2-(cyclohexenyl)ethyl, and 3-(cyclohexenyl)propyl groups.

In formula (I), the alkyleneoxy group having 2 to 4 carbon atoms represented by AO is an ethyleneoxy, propyleneoxy, or butyleneoxy group. AO is preferably an alkyleneoxy group having 2 to 3 carbon atoms, and more preferably an ethyleneoxy group or a mixture of an ethyleneoxy and a propyleneoxy (propane-1,2-diyloxy) groups. To produce a carboxylic acid compound by catalytic oxidation, the terminal hydroxy group is preferably primary. Further, the farthest AO group from R is preferably an ethyleneoxy group. From the viewpoints of foaming properties and feeling in use, an average addition mole number of alkyleneoxy groups is preferably 1 to 50, more preferably 1 to 20, and even more preferably 1 to 10.

The salt of polyoxyalkylene alkyl ether carboxylic acid produced from the polyoxyalkylene alkyl ether compound represented by formula (I) by the method of the present invention has a structure represented by formula (II):

$$\{RO\text{-}(AO)_{n-1}\text{-}A'\text{-}COO\}_m M \qquad (II)$$

wherein, R, AO, and n represent the same meanings as in formula (I); A' represents an alkylene group having 1 to 3 carbon atoms; M represents a cation; and m represents the number equal to a valence number of M.

Preferred embodiments for R, AO, and n in formula (II) are the same as in formula (I). Examples of the cation referred to as M include a hydrogen ion, alkali metal ions, and alkaline earth metal ions. Examples of the alkali metal ion include lithium ion, sodium ion and potassium ion. Examples of the alkaline earth metal include magnesium ion and calcium ion. A' represents an alkylene group having 1 to 3 carbon atoms. The structure of -A'-COO— is formed by oxidation of the terminal -AO— of formula (I). A' thus has a smaller carbon atom number by one than the terminal -AO—.

From the viewpoint of viscosity of a mixture during production, M preferably represents a hydrogen ion or an alkali metal ion. For convenience of the steps of production, M is more preferably an alkali metal ion. From the viewpoint of production cost, among alkali metal ions, preferred is a sodium or potassium ion.

Particularly when using the polyoxyalkylene alkyl ether represented by formula (I) in which AO represents an alkyleneoxy group having 2 carbon atoms (ethyleneoxy group), the salt of polyoxyalkylene alkyl ether carboxylic acid produced by the method of the present invention has a structure represented by the formula (II-1):

$$\{RO\text{—}(CH_2CH_2O)_{n-1}\text{—}CH_2\text{—}COO\}_m M \qquad (II\text{-}1)$$

wherein, R and n represent the same meanings as in formula (I); M represents a cation; and m represents the number equal to a valence number of M.

The total concentration of the salt of polyoxyalkylene alkyl ether carboxylic acid and the polyoxyalkylene alkyl ether in the liquid phase is preferably 1 to 30% by weight, more preferably 5 to 25% by weight, and even more preferably 10 to 23% by weight. The concentration is preferably controlled within this range in the continuous stirred tank reactor.

The noble metal catalyst used in the present invention preferably contains at least one selected from elements of the platinum group, concretely selected from ruthenium, rhodium, palladium, osmium, iridium, and platinum. It is more preferably selected from palladium and platinum.

The noble metal catalyst containing at least one element selected from the platinum group (hereinafter, referred to as a first catalyst component) preferably further contains at least one element as a catalyst component selected from tin, bismuth, selenium, tellurium, and antimony (hereinafter, referred to as a second catalyst component).

When the noble metal catalyst contains a first catalyst component and a second catalyst component, it can further contain at least one element as a catalyst component selected from rare earth elements (hereinafter, referred to as a third catalyst component).

The noble metal catalyst is preferably used in a supported form. The support is preferably inorganic. Examples of the support include activated charcoal, alumina, silica gel, activated clay, and diatomaceous earth. Among the supports, activated charcoal is preferred from the viewpoint of resistance against the alkali substance contained together in the reaction zone. A supported amount of the first catalyst component is preferably 0.1 to 20% by weight, more preferably 1 to 15% by weight, and even more preferably 2 to 13% by weight of a supported amount of the whole catalyst.

The noble metal catalyst used in the present invention can be produced according to known methods such as that described in JP-A 62-269746. For example, a compound containing an element of the first catalyst component (palladium chloride, platinum chloride, or the like) and a compound containing an element of the second catalyst component (bismuth chloride, antimony pentachloride, or the like), and, if needed, a compound containing an element of the third catalyst component (cerium chloride, lanthanum chloride, or the like) are adsorbed, in the form of aqueous solutions thereof, respectively, on a support such as activated charcoal and then are reduced to obtain a noble metal catalyst.

A molar ratio of the second catalyst component to the first catalyst component, second catalyst component/first catalyst component, is preferably 0.001 to 10, more preferably 0.005 to 7, and even more preferably 0.01 to 6. A molar ratio of the third catalyst component to the first catalyst component, third catalyst component/first catalyst component, is preferably 0.01 to 5.

A supported amount of the first catalyst component is preferably 0.1 to 20% by weight, more preferably 1 to 15% by weight, and even more preferably 2 to 13% by weight of the whole catalyst supported. In the case of the first catalyst component containing plural elements, the total of the elements is preferably within the above shown range for the supported amount. A supported amount of the second catalyst component is preferably 0.001 to 20% by weight, more preferably 0.01 to 15% by weight, and even more preferably 0.05 to 10% by weight of the whole catalyst supported. A supported amount of the third catalyst component is preferably 0.01 to 20% by weight, more preferably 0.05 to 15% by weight, and even more preferably 0.1 to 5% by weight of the whole catalyst supported. Also when the second catalyst component and the third catalyst component contain plural elements, respectively, the total amount of the elements of the second catalyst component and the total amount of the elements of the third catalyst component are preferably within the preferably ranges thereof, respectively.

The noble metal catalyst is preferably used in such amount as that an amount of the first catalyst component in the noble metal catalyst is 0.001 to 2.0% by weight, more preferably 0.01 to 1.5% by weight, and even more preferably 0.02 to 1.3% by weight to the polyoxyalkylene alkyl ether. In the case of the first catalyst component containing plural elements, the total of these elements is preferably within the range for the amount used.

In the case of the noble metal catalyst containing the first and the second catalyst components, the total amount of these components is preferably 0.001 to 4% by weight, and more preferably 0.01 to 3% by weight to the polyoxyalkylene alkyl ether.

In the case of the noble metal catalyst containing the first catalyst component, the second catalyst component and the third catalyst component, the total amount of the components is preferably 0.001 to 6% by weight, and more preferably 0.01 to 4% by weight to the polyoxyalkylene alkyl ether.

In the present invention, a continuous stirred tank reactor is preferably used for continuous oxidation of polyoxyalkylene alkyl ether with oxygen to produce a corresponding carboxylic acid by supplying polyoxyalkylene alkyl ether, an alkali material and oxygen into the liquid phase containing a noble metal catalyst. The reaction is controlled to have the molar ratio of the salt of polyoxyalkylene alkyl ether carboxylic acid to the polyoxyalkylene alkyl ether in the continuous stirred tank reactor within the range of 0.33 to 49, preferably 0.43 to 49, and more preferably 0.67 to 49. In the present invention, two or more continuous stirred tank reactors are preferably used in series. In production of the polyoxyalkylene alkyl ether carboxylic acid in two or more continuous stirred tank reactors in series, a liquid phase containing the polyoxyalkylene alkyl ether carboxylic acid at a constant concentration corresponding to the molar ratio 0.33 to 49 is supplied to a second reactor and the subsequent. In this case, for efficiently conducting the reaction in all the reactors, the molar ratio in the first continuous stirred tank reactor is preferably controlled to 0.33 to 0.67, and more preferably 0.37 to 1.0. Also in this case, the molar ratio in the last continuous stirred tank reactor is preferably 4 to 49, more preferably 4.9 to 49, and even more preferably 5.7 to 49. At the molar ratio not less than 4, the product can be easily purified, and not more than 49, the reaction will progress efficiently.

A reaction rate of the polyoxyalkylene alkyl ether in the continuous stirred tank reactor is controlled to 25 to 98%, preferably 30 to 98%, and more preferably 40 to 98%. As used herein, the "reaction rate" is a value defined by dividing a molar concentration of the polyoxyalkylene alkyl ether carboxylic acid in a reaction mixture by the total molar concentration of the polyoxyalkylene alkyl ether carboxylic acid and the polyoxyalkylene alkyl ether. In the present invention, two or more continuous stirred tank reactors are preferably used in series. In production of the polyoxyalkylene alkyl ether carboxylic acid with two or more continuous stirred tank reactors in series, to a second and the later reactors is supplied a liquid phase comprising the polyoxyalkylene alkyl ether carboxylic acid at a constant concentration corresponding to the reaction rate 25 to 98%. In this case, for efficiently conducting the reaction over the whole reactors, the reaction rate in the first continuous stirred tank reactor is preferably controlled to 25 to 60%, and more preferably 27 to 50%. Also in this case, the reaction rate in the last continuous stirred tank reactor is preferably 80 to 98%, more preferably 83 to 98%, and even more preferably 85 to 98%. At the reaction rate not less than 80%, the product can be easily purified, and not more than 98%, the reaction will progress efficiently.

In the present invention, the molar ratio of the salt of polyoxyalkylene alkyl ether carboxylic acid to the polyoxyalkylene alkyl ether and the reaction rate of the polyoxyalkylene alkyl ether in the continuous stirred tank reactor are preferably controlled within the respective ranges, concretely by controlling a flow rate of the polyoxyalkylene alkyl ether into the continuous stirred tank reactor, an amount of a reaction mixture in the continuous stirred tank reactor, and a flow rate of oxygen into the continuous stirred tank reactor. In the present invention, the liquid phase in the continuous stirred tank reactor is preferably maintained in a constant amount both by continuously supplying the polyoxyalkylene alkyl ether, the alkali material, and the noble metal catalyst to the liquid phase and extracting the liquid phase according to the supplied amount, and a constant composition is preferably maintained by supplying oxygen to the liquid phase to oxidize the polyoxyethylene alkyl ether.

Oxygen can be supplied to the liquid phase of each continuous stirred tank reactor by blowing oxygen gas or a oxygen-containing gas (e.g., air) into the liquid phase. In a continuous stirred tank reactor, a blowing rate can be adjusted such that a molar ratio of oxygen molecules is selected within the range of 0.1 to 2.0, and preferably within the range of 0.25 to 1.0 in accordance with the flow rate of the polyoxyalkylene alkyl ether supplied to the continuous stirred tank reactor.

In the present invention, a reaction temperature in oxidation of the polyoxyethylene alkyl ether with oxygen is preferably 50 to 90° C., and more preferably 60 to 80° C. For increasing a solubility of oxygen in a reaction mixture and from the viewpoint of pressure resistance of the reactor, a reaction pressure is preferably 0 (ambient pressure) to 1.0 MPa, and more preferably 0.1 to 0.5 MPa.

In the present invention, the polyoxyethylene alkyl ether is oxidized with oxygen in the continuous stirred tank reactor during stirring a liquid phase. An index of stirring efficiency $P_v$ is preferably not less than 0.1, more preferably not less than 0.5, and even more preferably not less than 2. The "$P_v$" value means a power consumption per unit volume of fluid, and is defined by a true stirring power acting on a liquid phase (kW), which is calculated by subtracting frictional losses from a stirring power of a stirrer, divided by a volume of a reaction liquid ($m^3$). The liquid phase can be stirred with a stirrer including a stirring impeller such as 3-sweptback blade impeller, Fullzone impeller, turbine impeller, and Maxblend impeller.

In the present invention, the polyoxyalkylene alkyl ether, the alkali material, the liquid phase, and the noble metal catalyst can be each charged continuously or intermittently in each continuous stirred tank reactor. The alkali material generally can be used in the form of aqueous solution. In this case, the alkali material may be charged continuously or intermittently so as to keep pH of the liquid phase at a predetermined value.

In the case of using a powder catalyst, a liquid phase provided from the last continuous stirred tank reactor contains the catalyst together with the polyoxyalkylene alkyl ether carboxylic acid. The catalyst is thus removed from the liquid phase by filtration or the like. The filtered liquid phase contains the polyoxyalkylene alkyl ether carboxylic acid dissolved therein in the form of a salt thereof, and can be used as it is as a solution of a surfactant after adjustment of pH, or decomposed with a mineral acid such as hydrochloric acid and subjected to extraction to obtain a free polyoxyalkylene alkyl ether carboxylic acid. In the case of using a catalyst in a fixed-bed in a continuous stirred tank reactor, the removal of the catalyst can be omitted.

In the present invention, the polyoxyalkylene alkyl ether carboxylic acid and a salt thereof are produced in the continuous stirred tank reactor at a controlled molar ratio of the salt of polyoxyalkylene alkyl ether carboxylic acid to the polyoxyalkylene alkyl ether to 0.33 to 49. The reaction mixture in the reactor is thus prevented from having an increased viscosity and can react without an induction period at the early state of the reaction. Therefore, the method of the present invention can efficiently produce the polyoxyalkylene alkyl ether carboxylic acid and a salt thereof with a high quality for a short time.

Besides the continuous stirred tank reactor, a flow tube reactor for continuous flow reaction is known. However, only the continuous stirred tank reactor can achieve the effects of the present invention. The "continuous stirred tank reactor" refers to a reaction system that conducts both continuous supply of a material to be reacted into a stirred tank and continuous extraction of a product from the stirred tank. Continuous supply of materials and continuous extraction of a product can be performed at a constant rate or in an intermittent way as long as the reaction composition does not change in the constant state in the stirred tank. In the flow tube reactor, a reaction progresses during flowing in a tube driven by a piston, as described in "Shinpan Kagaku Kougaku (new edition of chemical engineering)" (Society of Chemical Engineers eds., Maki Shoten, 1st edition, published on 1992, December). A reaction composition changes along with a direction of flowing like as a reaction in a batch mode progresses over the course of a reaction time. As thus, a part in a reaction mixture at which the reaction progresses to a low degree significantly exhibits high viscosity to cause problems in transportation, and also effects for shortening a reaction time cannot be achieved. In the invention production of the polyoxyalkylene alkyl ether carboxylic acid and a salt thereof by oxidizing the polyoxyethylene alkyl ether with oxygen, use of the continuous stirred tank reactor is considered to be advantageous to perform a process of the production, without a reaction composition having a molar ratio of the salt of polyoxyalkylene alkyl ether carboxylic acid to the polyoxyalkylene alkyl ether of less than 0.33, which may affect adversely the reaction, in the process.

An embodiment of the continuous stirred tank reactor can be operated in any mode in practice if an intended constant composition is formed in the reactor. A continuous run may start up by supplying raw materials to the reactor and taking a time to reach to the constant composition or by filling the reactor with a reactant at a composition similar to the constant composition to quickly reach to the steady state. In addition to the effects of the present invention, the continuous stirred tank reactor has an advantage such that multi-stage tanks are arranged in series in combination with each other and, in each reactor, a retention time, a flow rate of oxygen, and a reaction pressure are selected without limitation to provide a good productivity and a good quality.

In the method for producing the salt of polyoxyalkylene alkyl ether carboxylic acid of the present invention, catalytic oxidation of the polyoxyalkylene alkyl ether is conducted in the liquid phase containing the alkali material. Examples of the alkali material include alkali metal hydroxides such as sodium hydroxide and potassium hydroxide, alkaline earth metal hydroxides such as magnesium hydroxide and calcium hydroxide, alkali metal carbonates such as sodium carbonate and potassium carbonate, and alkaline earth metal carbonates such as magnesium carbonate and calcium carbonate. Among them, preferred are alkali metal hydroxides. From the viewpoints of reaction rate and color of the salt of polyoxyalkylene alkyl ether carboxylic acid generated, the alkali material is preferably supplied in such amount as that the liquid phase in the continuous stirred tank reactor has pH not less than 7.5, and more preferably pH 8 to 11. In the catalytic oxidation, the produced polyoxyalkylene alkyl ether carboxylic acid consumes the alkali. To perform the reaction at pH within the preferred range, the alkali is thus preferably supplied in a stoichiometric or larger amount to the consumption by the starting polyoxyalkylene ether in the reaction. In the case of using the alkali in an amount less than a stoichiometric amount to the polyoxyalkylene alkyl ether carboxylic acid produced, part of the product is present in the form of acid having formula (II) in which M represents a hydrogen ion.

In the method of the present invention, water is preferably used as a solvent. An organic solvent may also be used. In the method of the present invention, water generates and a concentration of water changes with progression of the reaction. A concentration of water in the liquid phase at the start of the catalytic oxidation is generally 0 to 99% by weight, preferably 0 to 90% by weight, and more preferably 0 to 70% by weight.

Oxygen can be supplied to the liquid phase by blowing oxygen gas or an oxygen-containing gas mixture (e.g., air) into the liquid phase. In the case of using the oxygen-containing gas mixture, specific examples of the gas combined with oxygen include common inert gases such as helium, argon, nitrogen, and carbon dioxide and hydrocarbons such as methane, ethane, and propane, which have no effect on the catalytic oxidation in the present invention (hereinafter, referred to as "inert gas of the present invention"). A concentration of oxygen in the gas blown is preferably not less than 10% by volume, and more preferably not less than 20% by volume. In particular, oxygen is preferably blown alone.

In the present invention, an amount of dissolved oxygen in the liquid phase in the continuous stirred tank reactor conducting the catalytic oxidation with oxygen supply is kept at the level more than 0 ppm and not more than 1 ppm, preferably not more than 0.8 ppm, and more preferably not more than 0.5 ppm. Within this range, the reaction will progress quickly and sufficiently to increase a reaction rate of the polyoxyalkylene alkyl ether.

In the method of the present invention, the catalytic oxidation can progress to saturation of conversion of the starting polyoxyalkylene alkyl ether or to a desired degree of the conversion. The reaction rate and the yield can be measured by gas chromatography or the like.

In the present invention, for keeping an amount of dissolved oxygen in the liquid phase at the level more than 0 ppm and not more than 1 ppm, the following methods can be employed:

(1) controlling a blowing rate of oxygen gas or oxygen-containing gas mixture;
(2) using an oxygen-containing gas mixture and controlling a concentration of oxygen in the gas mixture;
(3) blowing the inert gas of the present invention into the zone separately from oxygen gas and controlling a blowing rate of the inert gas;
(4) adding an additive that reacts with excess oxygen such as methanol, ethanol, propanol, formaldehyde, acetaldehyde, propionaldehyde, and hydrogen to the reaction mixture to control;
(5) controlling a pressure in the reaction zone; and
(6) Selecting a stirring impeller and controlling a stirring power. Among those methods, the method (1) is preferred.

In the present invention, a reaction temperature in the catalytic oxidation of the polyoxyalkylene alkyl ether is preferably 30 to 100° C., more preferably 40 to 90° C., and even more preferably 50 to 80° C. A reaction pressure, which may be the ambient pressure, is generally 0.03 to 0.5 MPa (gauge pressure, hereinafter simply referred to as "G"), preferably 0.05 to 0.4 MPa (G), and more preferably 0.07 to 0.3 MPa (G).

In the present invention, the catalytic oxidation of the polyoxyalkylene alkyl ether is preferably conducted in the stirred liquid phase. The liquid phase is preferably stirred with a stirring impeller such as 3-sweptback blade impeller, Fullzone impeller, turbine impeller, and Maxblend impeller.

After the reaction end, the catalyst is removed from the liquid phase by a method of solid-liquid separation such as centrifugation and filtration. In the liquid phase separated from the catalyst, the polyoxyalkylene alkyl ether carboxylic acid is dissolved in the form of salt with the alkali material. The liquid phase can be used as it is as a surfactant solution after pH adjustment if needed, or be converted to an acid with a mineral acid such as hydrochloric acid to obtain a free polyoxyalkylene alkyl ether carboxylic acid, or further neutralized with a hydroxide of an alkali metal or an alkaline earth metal, ammonia, or a lower alkanolamine to form a desired salt of the polyoxyalkylene alkyl ether carboxylic acid.

EXAMPLES

The following examples further describe and demonstrate embodiments of the present invention. The examples are given not to be construed as limitations of the present invention.

Example 1

To a 500 mL flask, supplied were a polyoxyalkylene alkyl ether having formula (I) in which R represented an alkyl group having 12 carbon atoms, AO represented an ethyleneoxy group, and n represented 5.5 at 17.8 g/h, 48% sodium hydroxide at 66.8 g/h, a slurry of 21.0% by weight catalyst (Pd 4%, Pt 1%, Bi 5%) in deionized water at 4.2 g/h, and air at ambient pressure at 25° C. (in the following Examples and Comparative Examples, air was always at ambient pressure and 25° C.) at 95.2 mL/min. A reaction mixture was continuously extracted from the flask so as to keep the amount of the reaction mixture in the flask to 219 mL. During the operations, a temperature of the reaction mixture was hold at 75° C., the reaction mixture was stirred at 385 rpm with a disc turbine impeller (width: 4.0 cm, height: 1.1 cm, six-impeller type), and a retention time of the reaction mixture in the flask was 2.5 hours. As a continuous stirred tank reactor, the reaction was started. After 10 hours, the reaction mixture in the reactor reached to a steady state with a constant composition. At this point, the reaction mixture was quantified by gas chromatography. The result showed that a reaction rate was 27% (a molar ratio of a salt of polyoxyalkylene alkyl ether carboxylic acid to the polyoxyalkylene alkyl ether was 0.37). In the steady state, a concentration of dissolved oxygen in the reaction mixture was measured with a dissolved oxygen meter (Horiba, Ltd., OM-51) and revealed to be at 0.0 ppm.

Comparative Example 1

In a 500 mL flask, introduced were 44.6 g of polyoxyalkylene alkyl ether having formula (I) in which R represented an alkyl group having 12 carbon atoms, AO represented an ethyleneoxy group, and n represented 5.5, 166.9 g of 48% sodium hydroxide, 10.5 g of slurry of 21.0% by weight catalyst (Pd 4%, Pt 1%, Bi 5%) in deionized water. To the flask, air was supplied at 95.2 mL/min and reacted. During the reaction, a temperature of the reaction mixture was hold at 75° C. and the reaction mixture was stirred at 385 rpm with a disc turbine impeller (width: 4.0 cm, height: 1.1 cm, six-impeller type). The flask served as a batchwise reactor. The reaction was started. After 2.5 hours, the reaction mixture was quantified by gas chromatography. The result showed that a reaction rate was 8.0% (a molar ratio of a salt of polyoxyalkylene alkyl ether carboxylic acid to the polyoxyalkylene alkyl ether was 0.087). At the end of the reaction, a concentration of dissolved oxygen in the reaction mixture was measured with a dissolved oxygen meter (Horiba, Ltd., OM-51) to be at 3.0 ppm.

Example 2

To a 500 mL flask, supplied were a polyoxyalkylene alkyl ether having formula (I) in which R represented a mixed alkyl group composed of 10% by mass of C10 alkyl, 80% by mass of C12 alkyl and 10% by mass of C14 alkyl, AO represented an ethyleneoxy group, and n represented 3.0 at 4.1 g/h, 48% sodium hydroxide at 21.9 g/h, a slurry of 15.8% by weight catalyst (Pd 4%, Pt 1%, Bi 5%) in deionized water at 1.3 g/h, and air at 95.2 mL/min. A reaction mixture was continuously extracted from the flask so as to keep the amount of the reaction mixture in the flask to 218 mL. During these operations, a temperature of the reaction mixture was hold at 75° C., the reaction mixture was stirred at 350 rpm with a disc turbine impeller (width: 4.0 cm, height: 0.8 cm, two six-impeller types), and a retention time of the reaction mixture in the flask was 7.9 hours. The flask served as a continuous stirred tank reactor. The reaction was started. After 20 hours, the reaction mixture in the reactor reached to a steady state with a constant composition. At this point, the reaction mixture was quantified by gas chromatography. The result showed that a reaction rate was 47% (a molar ratio of a salt of polyoxyalkylene alkyl ether carboxylic acid to the polyoxyalkylene alkyl ether was 0.89). At the steady state, a concentration of dissolved oxygen in the reaction mixture was measured with a dissolved oxygen meter (Horiba, Ltd., OM-51) and revealed to be at 0.0 ppm.

Comparative Example 2

In a 500 mL flask, introduced were 32.5 g of polyoxyalkylene alkyl ether having formula (I) in which R represented a mixed alkyl group composed of 10% by mass of C10 alkyl group, 80% by mass of C12 alkyl and 10% by mass of C14 alkyl, AO represented an ethyleneoxy group, and n represented 3.0, 173.2 g of 48% sodium hydroxide, 10.1 g of slurry of 15.8% by weight catalyst (Pd 4%, Pt 1%, Bi 5%) in deionized water. To the flask, air was supplied at 95.2 mL/min and the reaction was started. During the reaction, a temperature of the reaction mixture was hold at 75° C. and the reaction mixture was stirred at 350 rpm with a disc turbine impeller (width: 4.0 cm, height: 0.8 cm, two six-impeller types). As a batchwise reactor, the reaction was started. After 7.9 hours, the reaction mixture was quantified by gas chromatography. The result showed that a reaction rate was 9.0% (a molar ratio of a salt of polyoxyalkylene alkyl ether carboxylic acid to the polyoxyalkylene alkyl ether was 0.099). At the end of the reaction, a concentration of dissolved oxygen in the reaction mixture was measured with a dissolved oxygen meter (Horiba, Ltd., OM-51) and revealed to be at 1.1 ppm.

Example 3

To a new 500 mL flask, supplied were the extracted reaction mixture having a constant composition from the flask in Example 2 at the same flow rate to extraction (27.3 g/h) and air at 95.2 mL/min. A reaction mixture was continuously extracted from the flask so as to keep the amount of the reaction mixture in the flask to 218 mL. The reaction of a continuous stirred tank reactor of a second stage was conducted. During the operations, a temperature of the reaction mixture was hold at 75° C., the reaction mixture was stirred at 350 rpm with a disc turbine impeller (width: 4.0 cm, height: 0.8 cm, two six-impeller types), and a retention time of the reaction mixture in the flask was 7.9 hours. After 32 hours following to the start of the reactor running, the reaction mixture in the reactor reached to a steady state with a constant composition. At this point, the reaction mixture was quantified by gas chromatography. The result showed that a reaction rate was 85% (a molar ratio of a salt of polyoxyalkylene alkyl ether carboxylic acid to the polyoxyalkylene alkyl ether was 5.67). A measured color of the reaction mixture according to APHA was 229. At the steady state, a concentration of dissolved oxygen in the reaction mixture was measured with a dissolved oxygen meter (Horiba, Ltd., OM-51) to be at 0.4 ppm.

Comparative Example 3

In a 500 mL flask, introduced were 32.5 g of polyoxyalkylene alkyl ether having formula (I) in which R represented a mixed alkyl group composed of 10% by mass of C10 alkyl, 80% by mass of C12 alkyl and 10% by mass of C14 alkyl, AO represented an ethyleneoxy group, and n represented 3.0, 173.2 g of 48% sodium hydroxide, 10.1 g of slurry of 15.8% by weight catalyst (Pd 4%, Pt 1%, Bi 5%) in deionized water. To the flask, air was supplied at 95.2 mL/min and the reaction was started. During the reaction, a temperature of the reaction mixture was hold at 75° C. and the reaction mixture was stirred at 350 rpm with a disc turbine impellers (width: 4.0 cm, height: 0.8 cm, two six-impeller types). The flask served as a batchwise reactor. After 15.8 hours following to the start of the reactor running, the reaction mixture was quantified by gas chromatography. The result showed that a reaction rate was 13% (a molar ratio of a salt of polyoxyalkylene alkyl ether carboxylic acid to the polyoxyalkylene alkyl ether was 0.15). At the end of the reaction, a concentration of dissolved oxygen in the reaction mixture was measured with a dissolved oxygen meter (Horiba, Ltd., OM-51) to be at 1.5 ppm.

Comparative Example 4

In a 500 mL flask, introduced were 32.5 g of polyoxyalkylene alkyl ether having formula (I) in which R represented a mixed alkyl group composed of 10% by mass of C10 alkyl group, 80% by mass of C12 alkyl and 10% by mass of C14 alkyl, AO represented an ethyleneoxy group, and n represented 3.0, 173.2 g of 48% sodium hydroxide, 10.1 g of slurry of 15.8% by weight catalyst (Pd 4%, Pt 1%, Bi 5%) in deionized water. To the flask, air was supplied at 95.2 mL/min and reacted. During the reaction, a temperature of the reaction mixture was hold at 75° C. and the reaction mixture was stirred at 350 rpm with a disc turbine impeller (width: 4.0 cm, height: 0.8 cm, two six-impeller types). The flask served as a batchwise reactor. After 47 hours following to the start of the reactor running, the reaction mixture was quantified by gas chromatography. The result showed that a reaction rate was 82% (a molar ratio of a salt of polyoxyalkylene alkyl ether carboxylic acid to the polyoxyalkylene alkyl ether was 4.56). A measured color of the reaction mixture according to APHA was over 500. At the end of the reaction, a concentration of dissolved oxygen in the reaction mixture was measured with a dissolved oxygen meter (Horiba, Ltd., OM-51) and revealed to be at 3.0 ppm.

Results of Examples 1 to 3 and Comparative Examples 1 to 4 are shown in Table 1.

TABLE 1

|  | Example 1 | Comparative example 1 | Example 2 | Comparative example 2 | Example 3 | Comparative example 3 | Comparative example 4 |
| --- | --- | --- | --- | --- | --- | --- | --- |
| Starting materials | A | A | B | B | B | B | B |
| Reaction method | Continuous | Batchwise | Continuous | Batchwise | Continuous | Batchwise | Batchwise |
| Reactor | Stirred tank | Stirred tank | Stirred tank | Stirred tank | Stirred tank | Stirred tank | Stirred tank |
| Number of reactor | 1 | 1 | 1 | 1 | 2 | 1 | 1 |
| Reaction time(*1) | 2.5 Hr | 2.5 Hr | 7.9 Hr | 7.9 Hr | 15.8 Hr | 15.8 Hr | 47 Hr |
| salts of polyoxyalkylenealkylether carboxylic acid/ polyyoxyalkylene alkyl ether(molar ratio) | 0.37 | 0.087 | 0.89 | 0.099 | 5.67 | 0.15 | 4.56 |
| Reaction rate | 27% | 8.0% | 47% | 9.0% | 85% | 13% | 82% |
| Color (APHA)(*2) | — | — | — | — | 229 | — | >500 |

Starting material A: polyoxyalkylene alkyl ether having formula(I) in which R represented an alkyl group having 12 carbon atoms, AO represented an ethyleneoxy group, and R represented 5.5.
Starting material B: polyoxyalkylene alkyl ether having formula(I) in which R represented a mixed alkyl group composed of 10% by mass of C10 alkyl, 80% by mass of C12 alkyl and 10% by mass of C14 alkyl, AO represented an ethyleneoxy group, and n represented 3.0.
(*1)In the case of the continuous method, a reaction time was a retention time. In the case of using two or more reactors, a reaction time is the total of respective reaction periods of time in the stages.
(*2)A reaction rate and a color(APHA) were measured on a reation mixture provided from the reactor of the last stage.

The invention claimed is:

1. A method for producing a polyoxyalkylene alkyl ether carboxylic acid and a salt thereof, comprising continuously supplying polyoxyalkylene alkyl ether, oxygen, and water to a continuous stirred tank reactor in the presence of a noble metal catalyst in a reaction system that conducts both continuous supply of the materials into the stirred tank and continuous extraction of a product from the stirred tank to control the reaction in order to have the molar ratio of the salt of polyoxyalkylene alkyl ether carboxylic acid to the polyoxyalkylene alkyl ether in the reactor within the range of 0.33 to 49.

2. The method for producing polyoxyalkylene alkyl ether carboxylic acid and a salt thereof according to claim 1, wherein two or more continuous stirred tank reactors are used in series, and the reaction is controlled in order to have the molar ratio of the salt of polyoxyalkylene alkyl ether carboxylic acid to the polyoxyalkylene alkyl ether in a last continuous stirred tank reactor within the range of 0.33 to 49.

3. The method for producing polyoxyalkylene alkyl ether carboxylic acid and a salt thereof according to claim 1, wherein two or more continuous stirred tank reactors are used in series, and the reaction is controlled in order to have the molar ratio of the salt of polyoxyalkylene alkyl ether carboxylic acid to the polyoxyalkylene alkyl ether in a first continuous stirred tank reactor within the range of 0.33 to 0.67.

4. The method for producing polyoxyalkylene alkyl ether carboxylic acid and a salt thereof according to claim 1, wherein the polyoxyalkylene alkyl ether is a compound represented by formula (I):

$$RO\text{-}(AO)_n\text{-}H \qquad (I)$$

wherein, R represents a hydrocarbon group having 4 to 36 carbon atoms; AO represents an alkyleneoxy group having 2 to 4 carbon atoms; and n represents an average addition mole number of AO and a number of 1 to 100.

5. The method for producing polyoxyalkylene alkyl ether carboxylic acid and a salt thereof according to claim 1, comprising supplying the polyoxyalkylene alkyl ether, an alkali material, and the oxygen to a liquid phase containing a noble metal catalyst in the continuous stirred tank reactor.

6. The method for producing polyoxyalkylene alkyl ether carboxylic acid and a salt thereof according to claim 5, wherein the noble metal catalyst comprises at least one element selected from the group consisting of elements of the platinum group.

7. The method for producing polyoxyalkylene alkyl ether carboxylic acid and a salt thereof according to claim 5, wherein the noble metal catalyst is used in such an amount that the amount of a first catalyst component in the noble metal catalyst is 0.001 to 2.0% by weight to the polyoxyalkylene alkyl ether.

8. The method for producing polyoxyalkylene alkyl ether carboxylic acid and a salt thereof according to claim 5, wherein the alkali material is a compound selected from the group consisting of alkali metal hydroxides and alkali metal carbonates.

9. The method for producing polyoxyalkylene alkyl ether carboxylic acid and a salt thereof according to claim 1, wherein the polyoxyalkylene alkyl ether is oxidized with the oxygen at 50 to 90° C.

10. The method for producing polyoxyalkylene alkyl ether carboxylic acid and a salt thereof according to claim 1, wherein the amount of dissolved oxygen in the liquid phase in the continuous stirred tank reactor to which the oxygen is supplied is kept to be more than 0 ppm and not more than 1 ppm.

11. The method for producing polyoxyalkylene alkyl ether carboxylic acid and a salt thereof according to claim 1, wherein the amount of dissolved oxygen in the liquid phase in the continuous stirred tank reactor is kept to be more than 0 ppm and not more than 0.5 ppm.

12. The method for producing polyoxyalkylene alkyl ether carboxylic acid and a salt thereof according to claim 1, wherein the reaction is controlled to have the molar ratio of the salt of polyoxyalkylene alkyl ether carboxylic acid to the polyoxyalkylene alkyl ether in the continuous stirred tank reactor within the range of 0.43 to 49.

13. The method for producing polyoxyalkylene alkyl ether carboxylic acid and a salt thereof according to claim 2, wherein the reaction is controlled to have the molar ratio of the salt of polyoxyalkylene alkyl ether carboxylic acid to the polyoxyalkylene alkyl ether in the last continuous stirred tank reactor is 4 to 49.

14. The method for producing polyoxyalkylene alkyl ether carboxylic acid and a salt thereof according to claim 1, wherein two or more continuous stirred tank reactors are used in series and a liquid phase containing a salt of polyoxyalkylene alkyl ether carboxylic acid is supplied at a constant rate to a second and subsequent reactor to correspond to the molar ratio of the salt of polyoxyalkylene alkyl ether carboxylic acid to the polyoxyalkylene alkyl ether within the range of 0.33 to 49.

15. The method for producing polyoxyalkylene alkyl ether carboxylic acid and a salt thereof according to claim 1, wherein R in the polyoxyalkylene alkyl ether carboxylic acid is a compound represented by formula (I) has 10 to 14 carbon atoms.

16. The method for producing polyoxyalkylene alkyl ether carboxylic acid and a salt thereof according to claim 5, wherein the noble metal catalyst is used in such an amount that the amount of a first catalyst component in the noble metal catalyst is 0.01 to 1.5% by weight to the polyoxyalkylene alkyl ether.

* * * * *